US008778616B2

(12) United States Patent
Ambati et al.

(10) Patent No.: US 8,778,616 B2
(45) Date of Patent: *Jul. 15, 2014

(54) METHOD OF USING CCR3 BINDING AGENTS TO DETECT CHOROIDAL NEOVASCULARIZATION

(75) Inventors: Jayakrishna Ambati, Lexington, KY (US); Mark Ellsworth Kleinman, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/322,087

(22) PCT Filed: May 26, 2010

(86) PCT No.: PCT/US2010/036202
§ 371 (c)(1),
(2), (4) Date: Nov. 22, 2011

(87) PCT Pub. No.: WO2010/138591
PCT Pub. Date: Dec. 2, 2010

(65) Prior Publication Data
US 2012/0064010 A1 Mar. 15, 2012

Related U.S. Application Data

(60) Provisional application No. 61/181,161, filed on May 26, 2009.

(51) Int. Cl.
G01N 33/53 (2006.01)
G01N 33/567 (2006.01)

(52) U.S. Cl.
USPC ............ 435/7.1; 435/7.21; 977/774; 977/927

(58) Field of Classification Search
None
See application file for complete search history.

(56) References Cited

U.S. PATENT DOCUMENTS

| 6,207,155 | B1 | 3/2001 | Grimaldi et al. | |
|---|---|---|---|---|
| 6,420,424 | B1 | 7/2002 | Dhanak et al. | |
| 6,566,376 | B1 | 5/2003 | Baxter et al. | |
| 6,806,061 | B1 | 10/2004 | Gerard et al. | |
| 2002/0147312 | A1 | 10/2002 | O'Keefe et al. | |
| 2004/0234505 | A1* | 11/2004 | Naylor et al. | 424/93.2 |
| 2005/0069955 | A1 | 3/2005 | Plaksin et al. | |
| 2005/0191702 | A1 | 9/2005 | Mack et al. | |
| 2009/0110633 | A1 | 4/2009 | Sengupta et al. | |
| 2009/0123375 | A1* | 5/2009 | Ambati | 424/9.1 |

OTHER PUBLICATIONS

Salcedo R, et al. J. Immunol., 166:7571-7578, 2001. (http://www.jimmunol.org/content/166/12/7571).*
Takeda A, et al. Nature, 460(7252):225-230, Jul. 9, 2009. (doi: 10.1038/nature08151).*
PCT International Search Report of PCT/US10/36202.
International Preliminary Report on Patentability and Written Opinion of PCT/US10/36202.
Aird, WC, "Mechanisms of endothelial cell heterogeneity in health and disease", *Circ Res* 2006, 98:159-162.
Hendrickx et al., "Molecular diversity of cardiac endothelial cells in vitro and in vivo", *Physiol Genomics* 2004, 19:198-206.
Hwang et al., "Aniogenic Activity of Human CC Chemokine CCL15 in Vitro and in Vivo", FEBS Letters, 2004, 570:47-51.
Lang et al., "Differential mitogenic responses of human macrovascular and microvascular endothelial cells to cytokines underline their phenotypic heterogeneity", *Cell Prolif* 2001, 34:143-155.
Langenkamp et al., "Microvascular endothelial cell heterogeneity: general concepts and pharmacological consequences for antiagiogenic therapy of cancer", *Cell Tissue Res* 335:205-222 (2009).
Mason et al., "Human umbilical vein and dermal microvascular endothelial cells show heterogeneity in response to PKC activation", *Am J Physiol Cell Physiol*, 1997, 273:1233-1240.
Oh et al., "Subtractive proteomic mapping of the endothelial surface in lung and solid tumours for tissue-specific therapy", *Nature* 2004, 429:629-635.
Shin et al. "Isolation of arterial-specfic genes by subtractive hybridization reveals molecular heterogeneity among arterial endothelial cells", *Developmental Dynamics*, 2005, 233:1589-1604.
Smith et al., "Unique gene expression profiles of donor-matched human retinal and choroidal vascular endothelial cells", *Investigative Ophtal & Visual Sci* 2007, vol. 48, No. 6, pp. 2676-2684.
St. Croix et al., "Genes Expressed in Human Tumor Endothelium", *Sci* 2000, 289, 1197-1202.
Stevens, Troy, "Molecular and Cellular Determinants of Lung Endothelial Cell Heterogeneity", *Chest* 128:558S-564S (2005).
Thorin et al., "Heterogeneity of vascular endothelial cells in normal and disease states", *Pharmacol Ther* 1998, vol. 78, No. 3, pp. 115-166.
Wallace et al., The Role of Chemokines and Their Receptors in Ocular Disease, *Prog Retin Eye Res.*, 23:435-448.

(Continued)

Primary Examiner — Robert Landsman
(74) Attorney, Agent, or Firm — Crowell & Moring LLP (57) ABSTRACT

The results presented herein demonstrate the specific expression of CCR3 in CNV endothelial cells in humans with AMD, and despite the expression of its ligands, eotaxin-1, -2, and -3, neither eosinophils nor mast cells are present in human CNV. The genetic or pharmacological targeting of CCR3 or eotaxins as disclosed herein inhibited injury-induced CNV in mice. CNV suppression by CCR3 blockade was due to direct inhibition of endothelial cell proliferation, and was uncoupled from inflammation as it occurred in mice lacking eosinophils or mast cells and was independent of macrophage and neutrophil recruitment. CCR3 blockade was more effective at reducing CNV than vascular endothelial growth factor-A (VEGF-A) neutralization, which is currently in clinical use, and, unlike VEGF-A blockade, not toxic to the mouse retina. In vivo imaging with CCR3-targeting quantum dots located spontaneous CNV invisible to standard fluorescein angiography in mice before retinal invasion. CCR3 targeting is useful in reducing vision loss due to AMD through early detection and therapeutic angioinhibition.

11 Claims, 11 Drawing Sheets

(56) References Cited

OTHER PUBLICATIONS

Yashima et al., "Heterogeneity of the signal transduction pathways for VEGF-induced MAPKs activation in human vascular endothelial cells", *J Cell Physiol* 2001, 188:201-210.

Zamora et al., Proteomic profiling of human retinal and chorodial endothelial cells reveals molecular heterogeneity related to tissue of origin, *Molecular Vision* 2007, 13:2058-2065.

Zhang et al., "In vivo differences between endothelial transcriptional profiles of coronary and iliac arteries revealed by micro array analysis", *American J Physiol Heart Circ. Physiol* 295:H1556-H1561 (2008).

Morris et al., "Age-related macular degeneration and recent developments: new hope for old eyes?", *Postgrad Med J*, 2007, 83:301-307.

Ding et al., "Molecular pathology of age-related macular degeneration", *Prog Retin Eyes Res*. Jan. 2009, 28(1): 1-18.

\* cited by examiner

Wild Type     $Ccl2^{-/-}\ Ccr2^{-/-}$

Fluorescein

FIG. 4b

QDot-Isotype Fab     QDot-CCR3 Fab

Baseline 1 h 4 h 12 h

METHOD OF USING CCR3 BINDING AGENTS TO DETECT CHOROIDAL NEOVASCULARIZATION

This application is a national stage of PCT International Application No. PCT/US2010/036202, filed May 26, 2010, which claims priority under 35 U.S.C. 119(e) to provisional application No. 61/181,161, filed May 26, 2009.

BACKGROUND

Age-related macular degeneration (AMD), a leading cause of blindness worldwide, is as prevalent as cancer in industrialized nations. Most blindness in AMD results from invasion of the retina by choroidal neovascularization (CNV). AMD affects 30-50 million people globally, with approximately 90% of severe vision loss attributed to CNV (Ambati, J., et al., Surv Ophthalmol. 48, 257-293 (2003)). The worldwide prevalence of CNV is expected to double in the next decade due to population aging. Targeting the pro-angiogenic cytokine vascular endothelial growth factor (VEGF)-A has been validated in patients with CNV (Gragoudas, et al. N Engl J. Med. 351, 2805-2816 (2004); Brown. et al. N Engl J. Med. 355, 1432-1444 (2006); Rosenfeld, et al. N Engl J. Med. 355, 1419-1431 (2006)). However, substantial improvement of vision occurs only in one-third of patients treated with VEGF-A antagonists, and one-sixth of treated patients still progress to legal blindness. Moreover, safety concerns with continual (Brown, et al. N Engl J. Med. 355, 1432-1444 (2006)) blockade of VEGF-A, which is constitutively expressed in the normal adult human retina Famiglietti et al. Brain Res. 969, 195-204 (2003)), are emerging Nishijima et al., Am J. Pathol. 171, 53-67 (2007); Saint-Geniez et al., PLoS ONE. 3, e3554 (2008)). Thus, treatment strategies based on more specific targeting of CNV are desirable. However, no molecular marker specific for human CNV has yet been reported.

BRIEF DESCRIPTION OF THE FIGURES

FIGS. 1a-j show that CCR3 and eotaxins are expressed in choroidal neovascularization. (a,b) Immunofluorescence shows that CCR3 receptor expression colocalizes with CD31$^+$ expressing blood vessels in surgically excised human AMD CNV tissue. Nuclei stained blue by DAPI. (b) Specificity of CCR3 staining is confirmed by absence of staining with isotype control IgG (a). (c,d) CCR3 is not immunolocalized in CD31$^+$ blood vessels (white arrowheads) in the choroid of patients with atrophic AMD who do not have CNV (c) or in aged patients without AMD (d). Autofluorescence of retinal pigmented epithelium (white arrow) and Bruch's membrane (asterisks) overlying choroid is seen (c,d). (e,f) CCR3 is not expressed in surgically excised avascular retinal fibrosis tissue (e) or in blood vessel of choroidal melanoma (f). (g-j) Immunohistochemistry shows expression of CCL11 (g), CCL24 (h), and CCL26 (i) in surgically excised AMD CNV tissue, primarily in the stroma (arrowheads) but also in the blood vessels (arrows). Specificity of staining is confirmed by absence of staining with isotype control IgG (j). Scale bars, 10 μm.

FIGS. 2a-f show CCR3 activation promotes angiogenesis. (a) Tube formation of primary human choroidal endothelial cells (CECs) in Matrigel in vitro was reduced by neutralizing anti-human CCR3 antibodies (Ab) compared to isotype IgG. n=6, *P<0.05 compared to isotype IgG. (b) Fraction of CD31+VEGFR2$^+$ gated mouse CECs in vivo in proliferative state (S phase) was increased 5 days after laser injury in wild-type mouse eyes compared to control (uninjured eyes), and was reduced by intraocular administration of neutralizing anti-mouse CCR3Ab compared to isotype IgG. n=6-10, *P<0.05 compared to IgG treatment. (c) Stimulation with eotaxins for 24 h induced human CEC proliferation. n=4, *P<0.05 compared to bovine serum albumin (BSA) treatment. (d,e) Stimulation with eotaxins, but not PBS, induced actin polymerization in human CECs. Relative F-actin content is expressed as the ratio of the mean channel fluorescence between eotaxin- and media alone-stimulated cells (d). Rhodamine-phalloidin staining shows F-actin fibre formation in eotaxin-stimulated cells (e). Nuclei stained blue by DAPI. Data representative of 3-4 independent experiments are shown. (c,e) CCL11 (10 ng/ml), CCL24 (100 ng/ml), CCL26 (2 μg/ml). (f) Stimulation with eotaxins for 16 hours induces dose-dependent migration of human CECs across 8 μm pore size Transwells. n=5-10, *P<0.05 compared to BSA treatment. (a-c, f) Significance by Mann-Whitney U test. Error bars depict s.e.m.

FIGS. 3a-j show that CNV is reduced by CCR3 or eotaxin ablation or blockade independent of leukocyte modulation. (a,b) Laser-induced CNV in wild-type mice was reduced by neutralizing anti-mouse CCR3Ab compared to isotype IgG (a) and by the CCR3 receptor antagonist (RA) SB328437 ((S)-Methyl-2-naphthoylamino-3-(4-nitrophenyl)propionate) compared to vehicle (PBS/DMSO) (b) in a dose-dependent fashion. n=8-12, *P<0.05 compared to no antibody or receptor antagonist. (c) Representative examples of CNV in drug-treated mice. (d) Laser-induced CNV was reduced in CCR3$^{-/-}$ mice compared to wild-type mice. n=9, *P<0.05 compared to wild-type mice. (e) Eotaxin-1 (Ccl-11) and eotaxin-2 (Ccl-24) protein levels, measured by ELISA, were increased following laser injury in wild-type mice. n=6, *P<0.05, #P<0.01 compared to 0 h baseline. (f) CCL-11 and CCL-24 immunofluorescence was localized in the retinal pigmented epithelial cell layer (arrows) adjacent to CD31$^+$ choroidal endothelial cells (arrowheads) on day 1 after laser injury in wild-type mice. Nuclei stained blue by DAPI. No specific immunofluorescence was detected with isotype control IgGs. Images representative of 3 independent experiments are shown. (g) Laser-induced CNV was reduced in CCL11$^{-/-}$ and in CCL24$^{-/-}$ mice compared to wild-type mice. n=8-10, *P<0.05 compared to wild-type mice. CNV is further reduced in CCL 11$^{-/-}$×CCL24$^{-/-}$ mice compared to single null mice. #P<0.05 compared to single null mice. (h) Laser-induced CNV in wild-type mice was reduced by neutralizing antibodies against mouse CCL11 or CCL24 compared to isotype IgG. n=7-10, *P<0.05 compared to no injection (control) or IgG. (i) Representative examples of CNV in eotaxin-neutralized mice. (j) Neutralizing anti-CCR3 antibodies (Ab) reduced laser-induced CNV in mice deficient in eosinophils (Δdbl GATA) or mast cells (Kit$^{w-v}$). n=6-9, *P<0.05 compared to IgG. Scale bars, (c,i), 100 μm; f, 20 μm. Error bars depict s.e.m.

FIGS. 4a-g demonstrate that CCR3-targeting quantum dots detect subretinal choroidal neovascularization (CNV). (a) Images of the fundus taken after intravenous injection of sodium fluorescein in wild-type and CCL2$^{-/-}$×CCRT$^{-/-}$ mice showed normal retinal vascular filling, but no areas of hyperfluorescence indicative of CNV. (b) After intravenous injection of QDot-CCR3 Fab in the same CCL2$^{-/-}$×CCR2$^{-/-}$ mouse shown in (a), focal branching choroidal hyperfluorescence was visualized (arrow) at 1 h in the same area that was not hyperfluorescent during fluorescein angiography (arrowhead in a). The intensity of this hyperfluorescence (shown in the inset) increased, attaining a peak at 4 h, and then declined in intensity but still persisted at 12 h. Corresponding images of QDot-Isotype Fab angiography showed no hyperfluorescence. (c-e) The region corresponding to the area of hyperfluorescence seen on QDot-CCR3Fab angiography in (b) contained multiple CD31+ blood vessels in the choroid (Ch) that were proliferating (Ki67+; arrows) and had not invaded the retina (Ret). Individual CD31+ (c), and Ki67+ (d), and merged (e) fluorescence channel images are shown. Arrows point to proliferating endothelial cells. Inset shows Ki67+ CD31+ cells in higher magnification. (f) QDot-CCR3Fab hyperfluorescent areas were localized to areas of subretinal CNV with CCR3+ endothelial cells. (g) The QDot label was visualized within CD31+ vasculature of subretinal CNV lesions. Images representative of 6 independent experiments. Scale bars, (c-e), 10 µm.

FIG. 5 shows that eotaxins activate Rac-1. Stimulation of human CECs with CCL11 (10 ng/ml), CCL24 (100 ng/ml), or CCL26 (2 µg/ml) increased levels of activate Rac-1 GTPase in human CECs compared to unstimulated (0 s) cells. Equal amounts (500 µg) of total cell lysates were probed for GTP-bound Rac-1 (active) by pull-down assays. Rac-1 and GAPDH immunoblotting were also performed using equal amounts (80 µg) of the original lysates to control for protein loading. Representative images of 3 independent experiments are shown.

FIGS. 7a-c show that CCR3 does not promote inflammation in mouse CNV model. (a) Laser injury did not recruit eosinophils ($CCR3^{hiCD3-}CD117^{intCD49d+}$) or mast cells ($CCR3^{intCD3-}CD117^{hiCD49d+}$) into the choroid. n=8. (b,c) Neutralizing anti-CCR3 Ab did not reduce infiltration of macrophages (Gr-1+F4/80−) 3 days after (b) or of neutrophils (F4/80+CD11c−) 1 day after (c) into the choroid following laser injury in wild-type mice. n=6. Macrophage and neutrophil index refer to the fraction of choroidal cells comprised of these inflammatory cells, normalized to value in PBS-treated eyes, at the peak of their infiltration (3 days for macrophages and 1 day for neutrophils).

FIG. 8 shows that CCR3 F(ab) Ab fragment detects CCR3 specifically. Thioglycolate-elicited cells obtained from wild type (WT) and Ccr3−/− mice were subjected to FACS analysis. SSChigh cells were electronically gated and assessed for SiglecF and CCR3 expression using the indicated antibodies. Eosinophil percentage (CCR3+/SiglecF+) is depicted in upper right corner of the dot-plot graph. Data are a representative experiment of n=4-6 mice per group. SSC, side scatter. SiglecF (Sialic acid-binding immunoglobulin-like lectin-F) is an eosinophil-prominent Siglec. SSC—H and FSH—C show the cell size and granularity and FL1-H and FL2-H show the staining intensity of the different antibodies used to stain cells.

FIG. 9 shows that CCR3 blockade is more effective at inhibiting CNV than VEGF-A blockade. A dose-ranging (0.5 ng-1 µg) study determined that the optimal dose of anti-VEGF-A neutralizing antibody (Ab) for inhibiting laser-induced CNV in wild-type mice when administered into the vitreous humor was 2 ng. The peak of CNV inhibition by VEGF-A neutralization was 57±4% compared to isotype control IgG, whereas anti-CCR3 neutralizing Ab, at an optimal dose of 1 µg, achieved an inhibition of 68±3% (☐$P<0.05$) compared to isotype control IgG. n=20–25.

FIGS. 10a-b show that CCR3 and VEGF-A do not modulate each other. (a) Intravitreous administration of anti-CCR3 neutralizing antibody (1 µg) following laser injury in wild-type mice did not change VEGF-A levels in the RPE/choroid 3 days after injury, compared to isotype control IgG (1 µg) administration. n=4. (b) Intravitreous administration of anti-VEGF-A neutralizing antibody (2 ng; gray curve) following laser injury in wild-type mice did not change surface CCR3 expression on CD31+VEGFR-2+ choroidal endothelial cells 5 days after injury compared to isotype control IgG (2 ng; black curve) administration. SFI, standardized fluorescence index (ratio of geometric means of cells exposed to control IgG (black curve) to cells exposed to anti-VEGF-A antibody (gray curve), n=3.

DESCRIPTION OF THE INVENTION

CCR3 Expression Restricted to CNV in Human Eyes

In our studies examining the role of chemokines in angiogenesis, we discovered that CCR3 (also known as CD193), a chemokine receptor best known for its role in promoting eosinophil and mast cell trafficking (Rothenberg and Hogan *Annu Rev Immunol.* 24, 147-174 (2006)), was expressed in human choroidal endothelial cells (CECs) only in the context of CNV due to AMD and not in other non-proliferating or proliferating choroidal vasculature (FIG. 1). Immunolocalization studies showed that CCR3 was expressed in CECs of all examined specimens of surgically excised CNV tissue from patients with AMD (18/18) who had received no prior treatment for AMD (FIG. 1a, b). In contrast, CCR3 was not expressed in CECs in the choroid of any patients with early (atrophic) AMD (0/10) or in age-matched patients without AMD (0/10) (FIG. 1c, d). CCR3 also was not immunolocalized in surgically excised tissue from patients with epiretinal fibrotic membranes (0/6) or in CECs in patients with choroidal melanoma (0/8) (FIG. 1e, f). Collectively these data point to a highly specific pattern of expression of CCR3 ($P=7 \times 10^{-14}$, exact contingency table test) in CECs in neovascular AMD. In addition, we identified the expression of the CCR3 ligands eotaxin-1 (CCL11), -2 (CCL24), and -3 (CCL26) in all examined specimens of surgically excised CNV tissue from patients with AMD who had received no prior treatment for AMD (FIG. 1g-j), suggesting that the eotaxin-CCR3 axis could play a role in this disease state. Interestingly, despite the abundance of eotaxins, eosinophils and mast cells were not identified in human CNV, consistent with earlier findings Grossniklaus et al. *Arch Ophthalmol.* 123, 914-921 (2005).

CCR3 Stimulation Promotes CEC Migration and Proliferation

The best elucidated pathological functions of CCR3 to date have been its role in allergic diseases such as asthma (Justice et al., *Am J Physiol Lung Cell Mol. Physiol.* 284, L169-178 (2003); Humbles. et al., *Science.* 305, 1776-1779 (2004); Pope et al., *J. Immunol.* 175, 5341-5350 (2005); Jose et al., *J Exp Med.* 179, 881-887 (1994); Teixeira et al., *J Clin Invest.* 100, 1657-1666 (1997)) and eosinophilic esophagitis (Blanchard et al., *J Clin Invest.* 116, 536-547 (2006). There is a single report of its direct role in angiogenesis Salcedo et al., *J. Immunol.* 166, 7571-7578 (2001)). Although eosinophils and mast cells have been reported to be involved in angiogenesis (Puxeddu et al., *Int J Biochem Cell Biol.* 37, 628-636 (2005); Heissig et al., *J Exp Med.* 202, 739-750 (2005)), such actions are considered minor or isolated. Therefore, we studied the effects of CCR3 modulation on angiogenesis in vitro and in vivo.

Figure 1A:
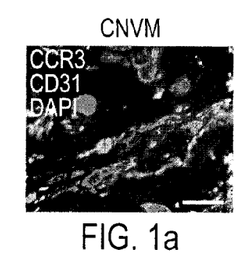
Figure 1B:
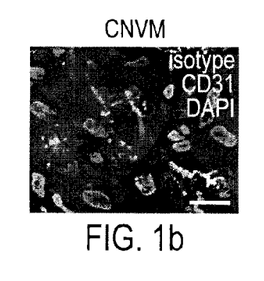
Figure 1C:
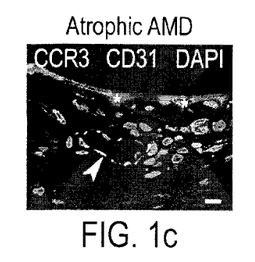
Figure 1D:
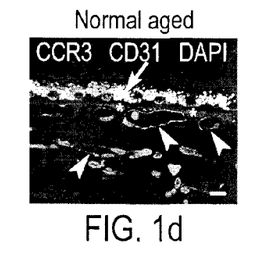
Figure 1E:
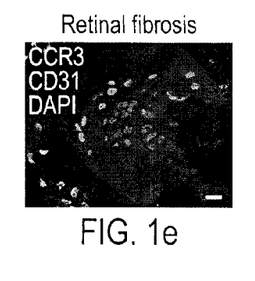
Figure 1F:
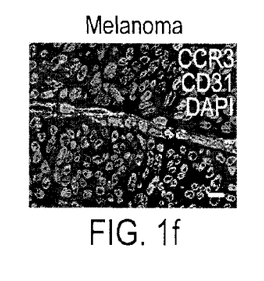
Figure 1G:
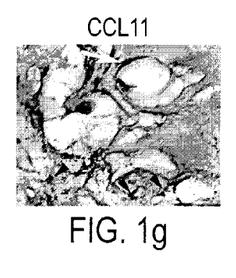
Figure 1H:
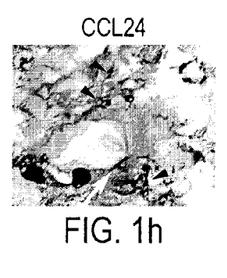
Figure 1I:
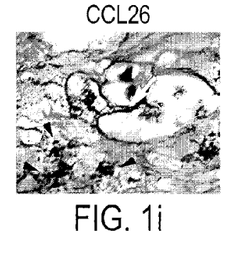
Figure 1J:
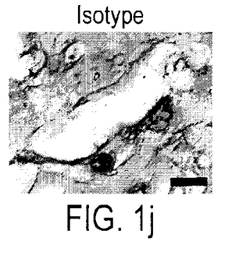
Figure 2A:
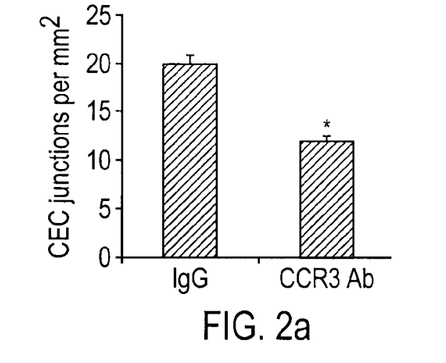
Figure 2B:
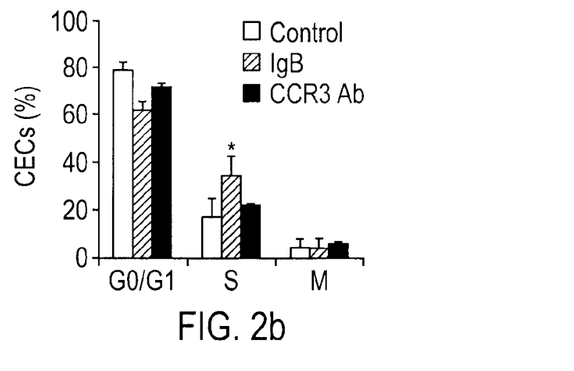
Figure 2C:
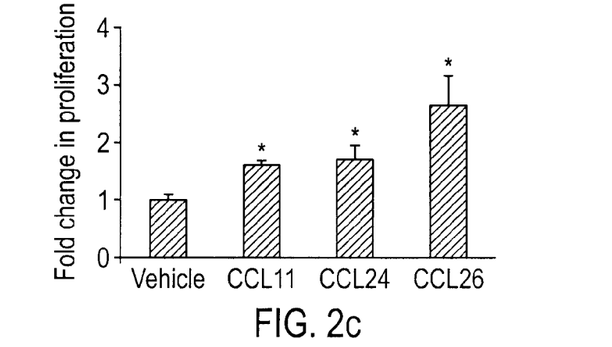
Figure 2D:
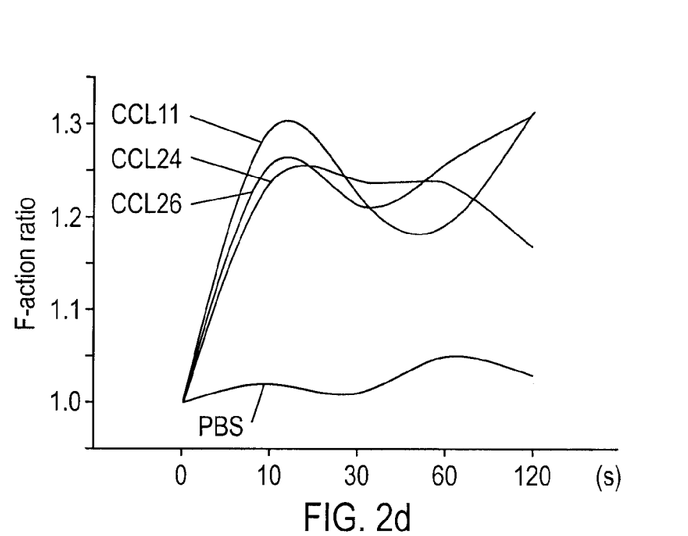
Figure 2E:
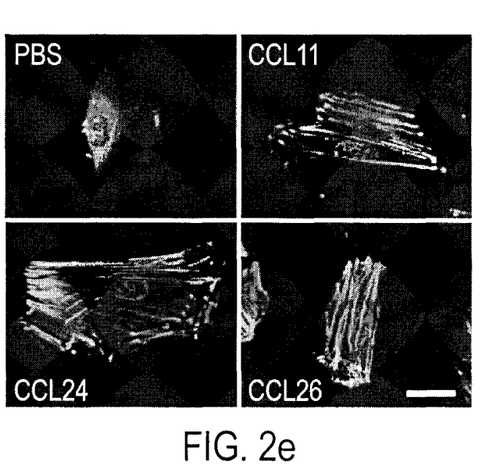
Figure 2F:
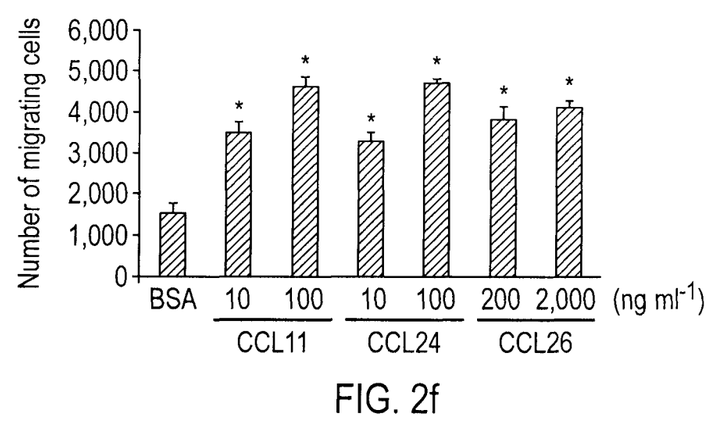
Figure 5:
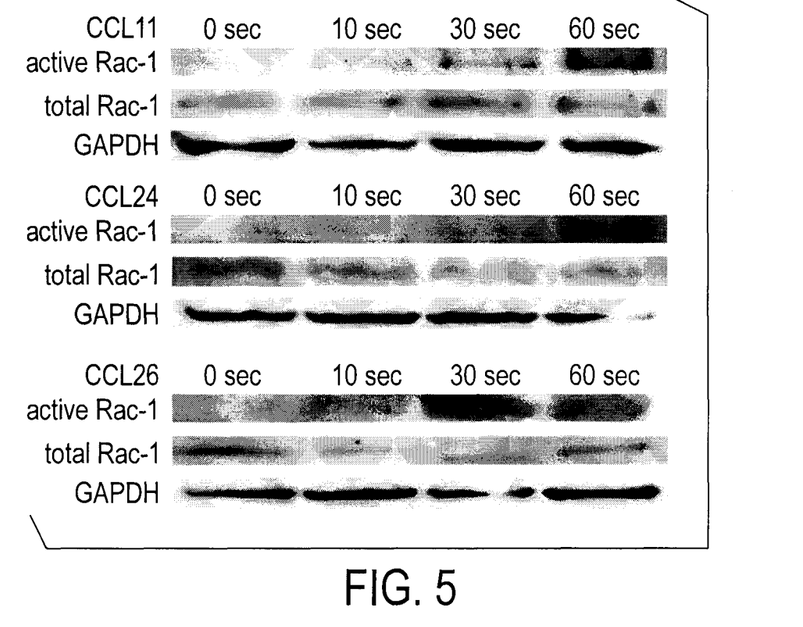

Neutralizing anti-CCR3 antibodies inhibited the tube formation of primary human CECs cultured in Matrigel in vitro (FIG. 2a). In an experimental model of CNV induced by laser injury in wild-type mice (Tobe et al., *Am J. Pathol.* 153, 1641-1646 (1998); Nozaki et al. *Proc Natl Acad Sci USA.* 103, 2328-2333 (2006); Nozaki et al., *J Clin Invest.* 116, 422-429 (2006); Kleinman et al., *Nature.* 452, 591-597 (2008); Sakurai et al., *Invest Ophthalmol V is Sci.* 44, 3578-3585 (2003); Sakurai et al. *Invest Ophthalmol Vis Sci.* 44, 2743-2749 (2003)), neutralizing anti-CCR3 antibodies reduced the fraction of CECs in vivo that were in the proliferative state of the cell cycle (FIG. 2b). Consistent with this finding, each of the three eotaxins stimulated human CEC proliferation (FIG. 2c). Cytoskeletal rearrangement through polymerization of monomeric actin to microfilamentous F-actin, which is essential for eosinophil chemotaxis induced by the eotaxins, is also critical in angiogenic migration of endothelial cells. Stimulation of human CECs with any of the three eotaxins induced a rapid polymerization of actin molecules (FIG. 2d, e). All three eotaxins also activated Rac-1 (FIG. 5), a small GTPase that is critical in regulating endothelial cell spreading and migration, and promoted human CEC migration in a dose-dependent fashion (FIG. 2f). Collectively these data demonstrate that CCR3 activation can promote multiple steps of angiogenesis. The expression of CCR3 on CECs in vivo is confined to CNV tissues; however, in vitro, human CECs responded to CCR3 ligands. Without wishing to be bound by theory, this might be due to the presence of several CNV-promoting growth factors in the culture medium.

CCR3 Receptor or Ligand Antagonism Inhibits CNV

Figure 3A:
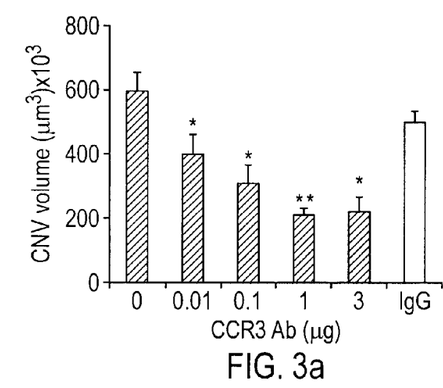
Figure 3B:
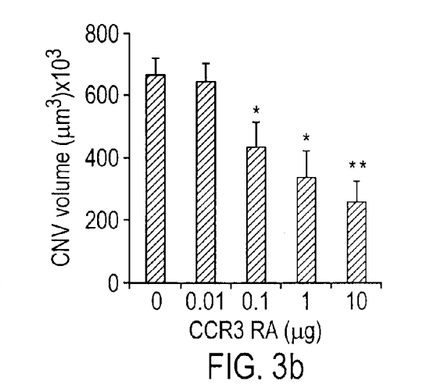
Figure 3C:
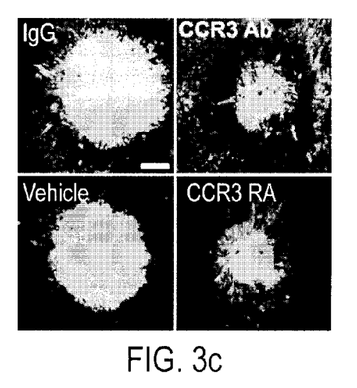
Figure 3D:
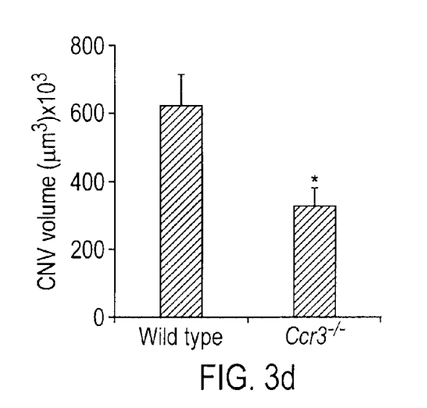
Figure 3E:
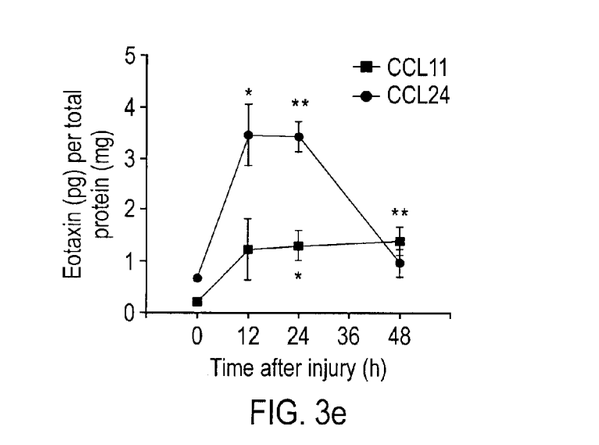
Figure 3F:
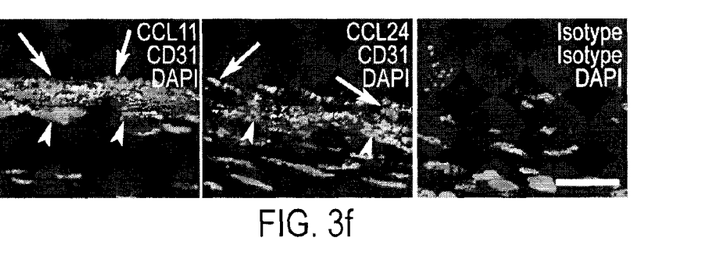
Figure 3G:
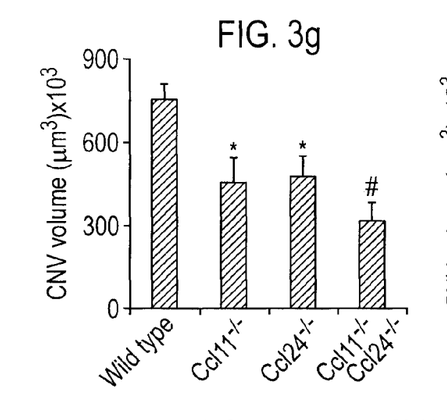
Figure 3H:
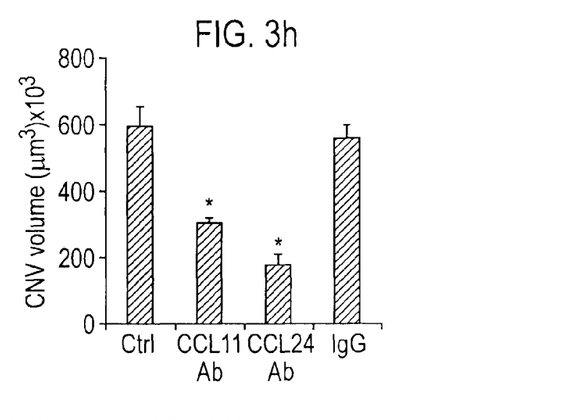
Figure 3I:
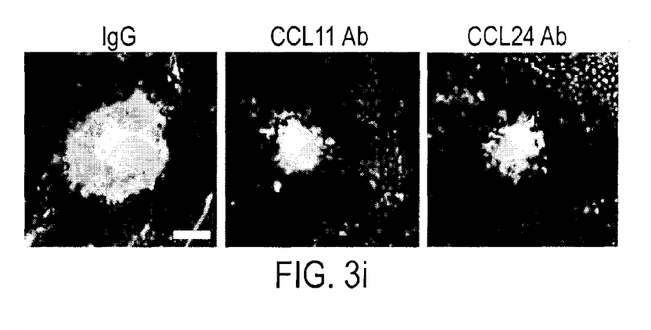
Figure 6:
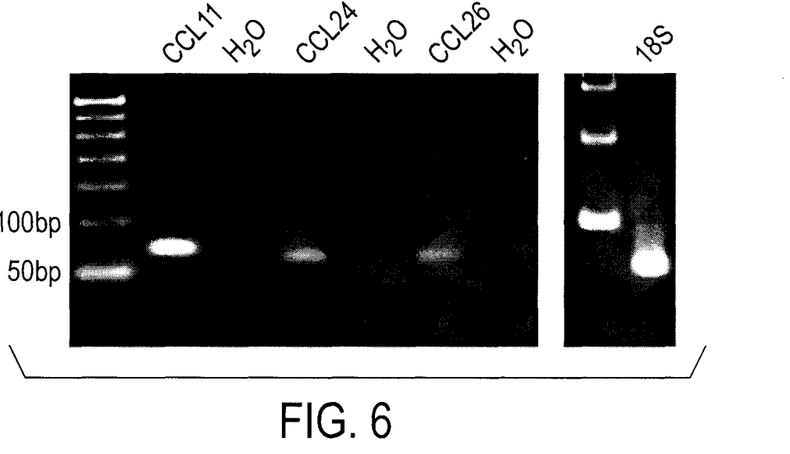
FIG. 6 shows that CCL11, CCL24, and CCL26 mRNA are expressed in cultured human RPE cells. Total RNA isolated from human RPE cells were subjected to RT-QPCR using specific primers for the three eotaxins or ribosomal 18S as control. Only one band with the predicted size was observed for each gene, and not in the corresponding negative control ($H_2O$).

We studied the in vivo effects of CCR3 targeting in a mouse model of CNV induced by laser injury (Kleinman et al., *Nature.* 452, 591-597 (2008)), which is the most widely utilized animal model of this disease. A single intraocular administration of either CCR3 neutralizing antibodies or a small molecule CCR3 receptor antagonist ((S)-Methyl-2-naphthoylamino-3-(4-nitrophenyl)propionate) both suppressed laser injury-induced CNV in wild-type mice in a dose-dependent fashion (FIG. 3a-c). CNV was also diminished in $Ccr3^{-/-}$ mice (Humbles et al., *Proc Natl Acad Sci USA.* 99, 1479-1484 (2002)) as compared to wild-type mice (FIG. 3d). The specificity of pharmacological CCR3 blockade was confirmed by demonstrating that CNV was not reduced in $Ccr3^{-/-}$ mice by CCR3 neutralizing antibodies or CCR3 receptor antagonist (116±7% and 109±16% of control, respectively; n=5; P>0.1). CCL-11 and CCL-24, the principal mouse ligands for CCR3, were markedly increased soon after laser injury and immunolocalized to the retinal pigmented epithelium (RPE), which is adjacent to CECs (FIG. 3e, f). Also, human RPE cells synthesized all three eotaxins (FIG. 6), implicating these cells, which are abundantly interspersed in CNV (Grossniklaus et al. *Arch Ophthalmol.* 123, 914-921 (2005)), as a source of CCR3 ligands in CNV. Genetic ablation of either Ccl11 (Rothenberg, et al., *J Exp Med.* 185, 785-790 (1997)) or Ccl24 (Pope et al., *J. Immunol.* 175, 5341-5350 (2005) reduced CNV, while the neovascular response in $Ccl11^{-/-} \times Ccl24^{-/-}$ mice (Pope et al. (2005) supra) was suppressed to a greater extent than in either of the "single knockout" mice, suggesting cooperation between these two ligands in this system (FIG. 3g). A single intraocular administration of neutralizing antibodies against CCL-11 or CCL-24 also suppressed CNV in wild-type mice (FIG. 3h, i), validating these CCR3 ligands as anti-angiogenic targets. Together, these data demonstrate that CCR3 activation is essential for in vivo angiogenesis in the most widely used preclinical model of neovascular AMD.

CCR3-Driven Angiogenesis Uncoupled from Inflammation

Figure 3J:
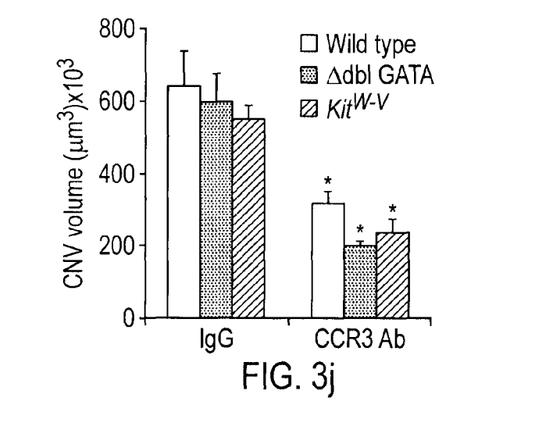
Figure 7A:
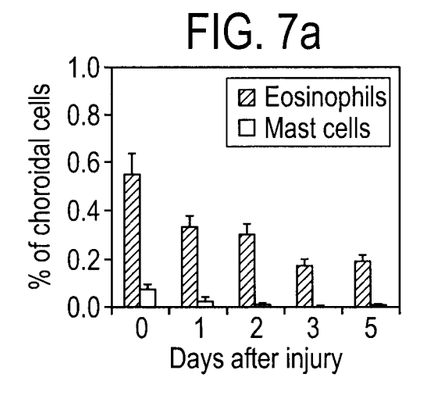
Figure 7B:
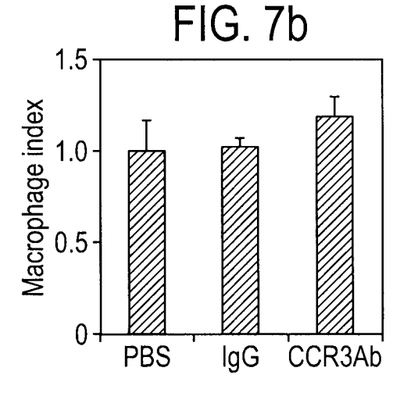
Figure 7C:
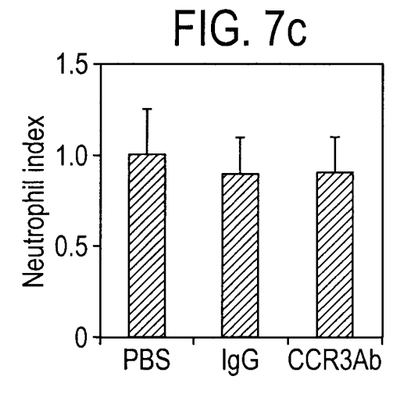

We sought to determine whether CCR3 targeting reduced CNV solely via anti-angiogenic mechanisms or whether anti-inflammatory mechanisms also were involved. Neither eosinophils nor mast cells (defined as $CCR3^{hi}CD3^- CD117^{int}CD49d^+$ and $CCR3^{int}CD3^-CD117^{hi}CD49d^+$ cells, respectively) were recruited to the choroid following laser injury, as monitored by flow cytometry (FIG. 7). Furthermore, the CNV response in eosinophil-deficient Δdbl GATA mice (Humbles et al., *Science.* 305, 1776-1779 (2004)) and mast cell-deficient $Kit^{W-v}/Kit^{W-v}$ mice (Kitamura et al., *Blood.* 52, 447-452 (1978)) was not different from that in wild-type mice (FIG. 3j). In addition, intraocular administration of neutralizing anti-CCR3 antibodies reduced CNV in Δdbl GATA or $Kit^{W-v}/Kit^{W-v}$ mice to the same extent as in wild-type mice. Thus, although eosinophils and mast cells have been reported to be capable of driving angiogenesis in other systems (Puxeddu et al., *Int J Biochem Cell Biol.* 37, 628-636 (2005); Heissig et al., *J Exp Med.* 202, 739-750 (2005), both cell types are dispensable in the development of experimental CNV. Although neutrophil and macrophage infiltration are crucial for the development of experimental CNV (Sakurai et al. (2003) supra; Zhou et al. *Mol. Vis.* 11, 414-424 (2005), CCR3 receptor targeting did not affect recruitment of either inflammatory cell type (defined as $Gr-1^+F4/80^-$ and $F4/80^+CD11c^-$ cells, respectively) (FIG. 7). Therefore, the angioinhibitory effect of CCR3 blockade in this model is a direct anti-vascular effect and does not appear to involve modulation of cellular inflammation. The mechanisms underlying the paucity of eosinophils and mast cells in CNV remain to be defined. While not wishing to be bound by theory, one explanation could be the expression of CXCL9, which blocks eotaxin-induced CCR3-mediated eosinophil recruitment (Fulkerson et al., *Proc Natl Acad Sci USA.* 101, 1987-1992 (2004); Fulkerson et al. *Blood.* 106, 436-443 (2005) in CNV. Other mechanisms influencing adhesion or mobilization of these leukocytes also might be operative.

CNV Bioimaging by Ccr3 Targeting

Figure 8:
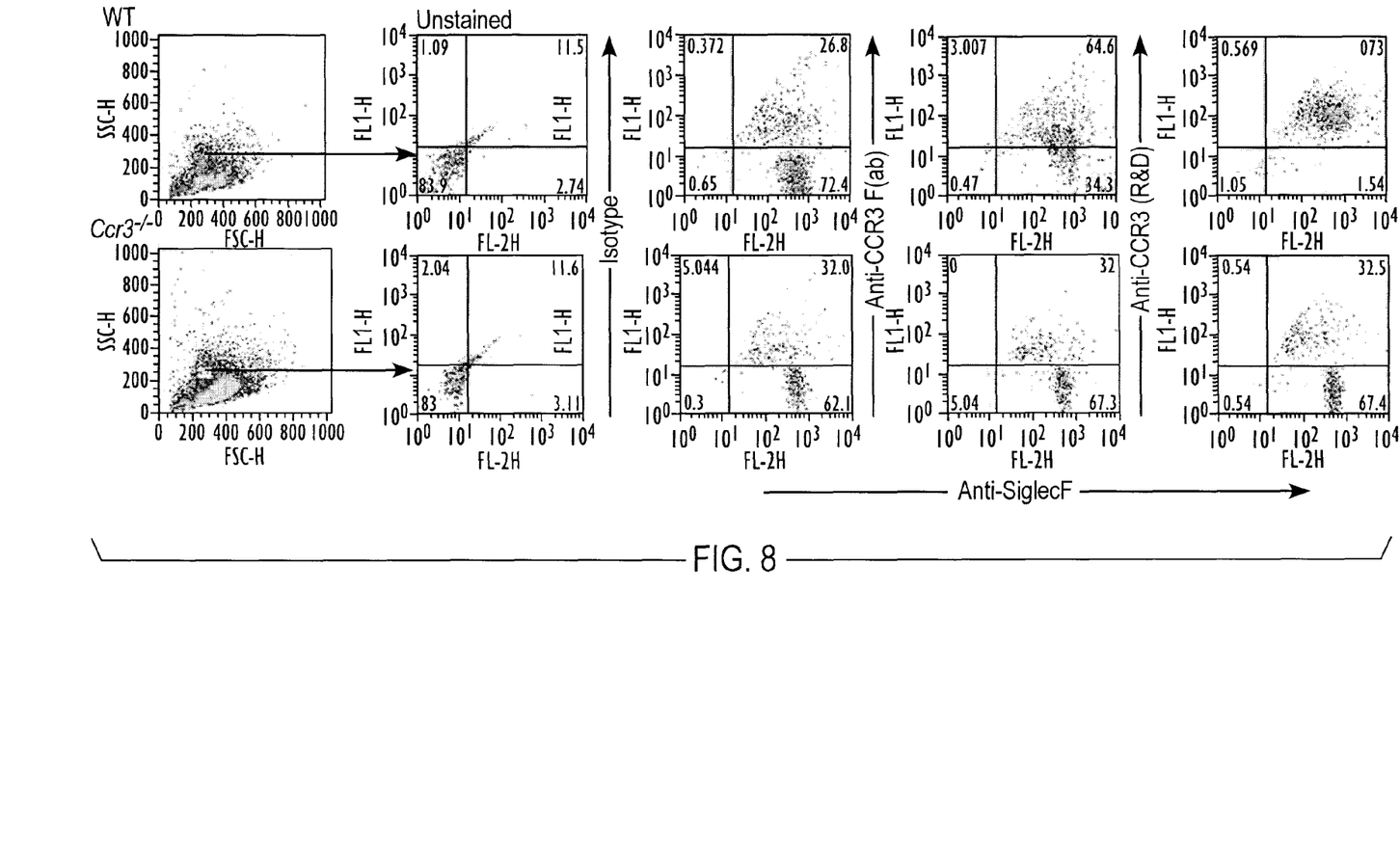

Because invasion of the retina by CNV results in morphological and functional disruption of the retina, early detection of CNV is desirable; indeed, detection of CNV before retinal invasion would be ideal. CNV that has breached the retina can be detected by fluorescein angiography. However, this diagnostic modality cannot detect CNV before it has invaded the retina, i.e., when it is still limited to the choroid. Yet postmortem histopathological studies have shown that substantial numbers of patients in whom fluorescein angiography does not reveal the presence of CNV nevertheless have CNV that has not yet invaded the retina (Green and Key, *Trans Am Ophthalmol Soc.* 75, 180-254 (1977). Therefore, we explored whether CCR3-targeted bioimaging using anti-CCR3 Fab antibody fragments (FIG. 8) conjugated to quantum dots (QDot-CCR3 Fab) could detect CNV before it became clinically evident.

Figure 4A:
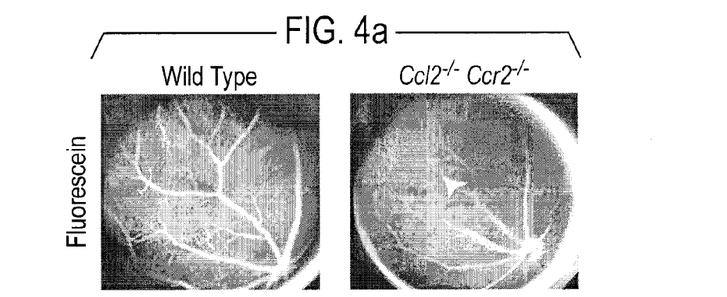
Figure 4B:
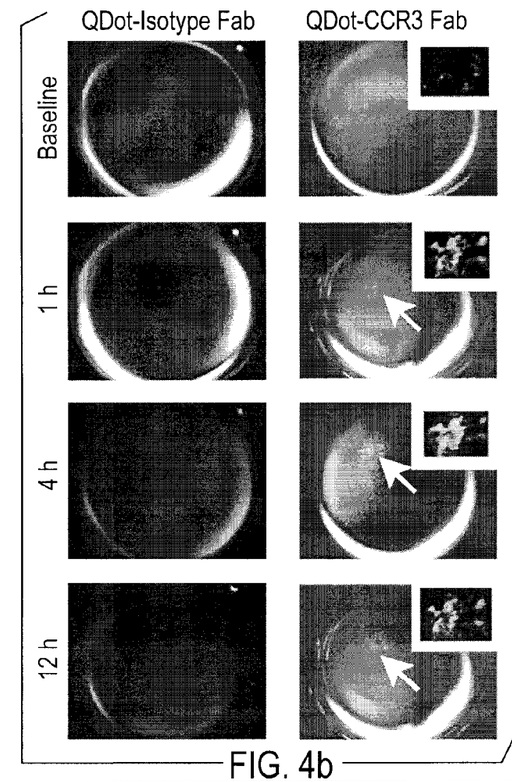
Figure 4C:
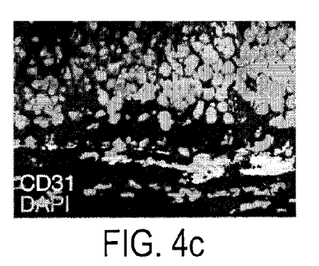
Figure 4D:
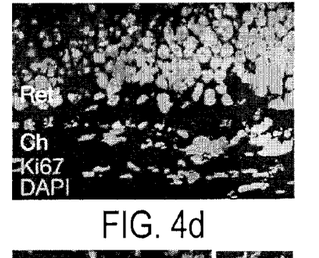
Figure 4E:
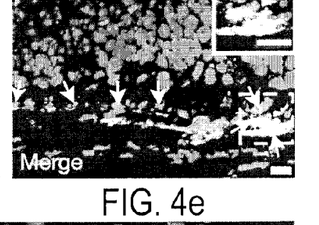
Figure 4F:
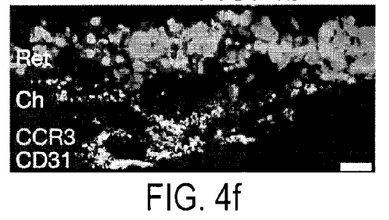
Figure 4G:
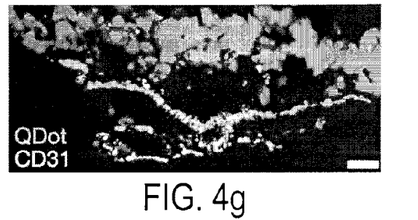

We previously described the spontaneous development of CNV in senescent mice deficient in monocyte chemoattractant protein-1 (MCP-1/CCL-2) or its CCR2 receptor (Ambati et al., *Nat. Med.* 9, 1390-1397 (2003)). Similar pathology occurs at a younger age in $Ccl2^{-/-} \times Ccr2^{-/-}$ mice (unpublished data). These mice also undergo outer retinal degeneration rapidly. We tested whether fundus angiography following intravenous injection of QDot-CCR3 Fab could detect subretinal CNV in these mice. QDot-CCR3 Fab angiography demonstrated hyperfluorescent signals in regions of the fundus of these mice that were silent on fluorescein angiography (FIG. 4a,b). The specificity of CCR3 targeting was confirmed by the absence of hyperfluorescent signals in Ccl2$^{-/-}$× Ccr2$^{-/-}$ mice injected with QDot-isotype Fab and in wild-type mice injected with QDot-CCR3 Fab (FIG. 4b). Histological examination of these areas revealed proliferating (Ki67$^+$) CCR3$^+$ blood vessels in the choroid that had not yet invaded the retina, along with accumulation of QDot-CCR3 Fab in these vessels (FIG. 4c-e). These data demonstrate that CCR3-targeted bioimaging can detect subclinical CNV before it disrupts the retina and causes vision loss.

CCR3 Targeting Superior to VEGF-A Targeting

Figure 9:
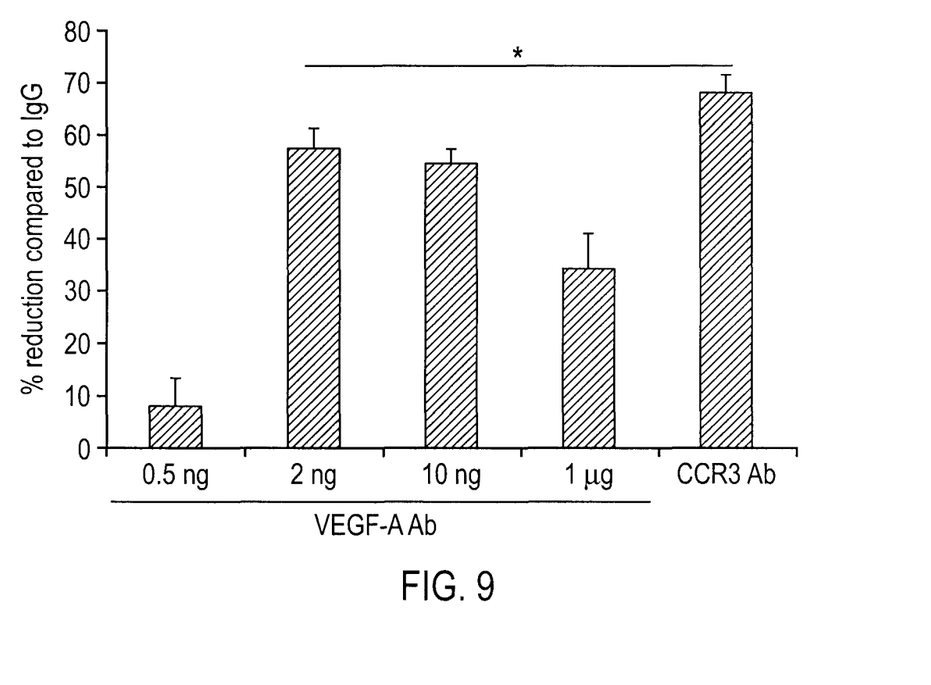
Figure 10A:
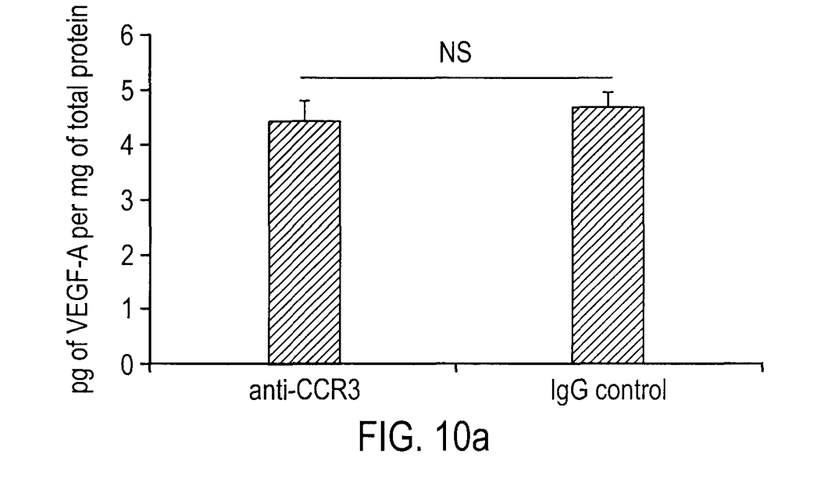
Figure 10B:
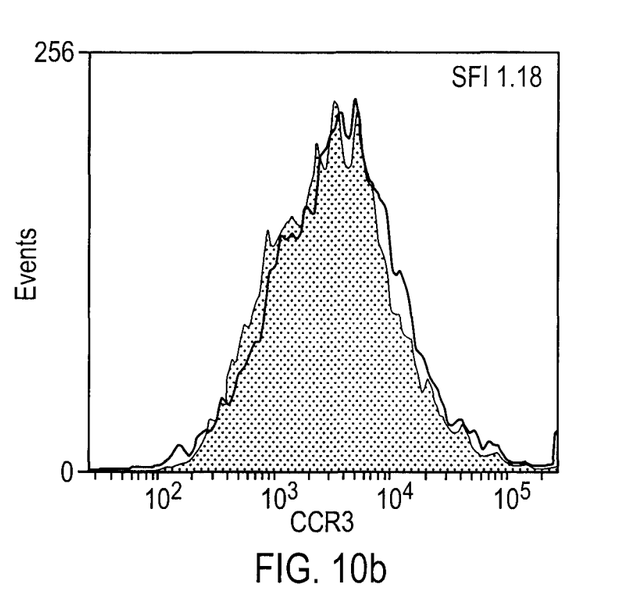

In comparing CCR3 targeting to VEGF-A targeting, the most effective approved treatment for human CNV, we found that CCR3 neutralizing antibodies were more effective than VEGF-A neutralizing antibodies (68±3% vs. 57±4%) at inhibiting laser-induced CNV in mice (FIG. 9). In the laser injury model, CCR3 neutralization did not change VEGF-A levels in the RPE/choroid and VEGF-A blockade did not change CCR3 expression on CECs (FIG. 10): these two pathways appear to be not directly coupled. Repeated intravitreous administration of anti-VEGF-A antibodies resulted in anatomic and functional damage to the retina in wild-type mice, consistent with earlier reports that anti-VEGF-A therapy induces dysfunction in and damage to the inner and outer murine retina[6,7]. These effects were modest at a dose of anti-VEGF-A antibodies that suppressed mouse CNV but more pronounced at a higher dose that is comparable to the dose used in humans. It should be noted that anti-VEGF-A pharmacotherapy has not been associated with an increased risk of profound retinal damage in humans (Ip et al., *Ophthalmology*. 115, 1837-1846 (2008), but subtle abnormalities have been observed (Sayanagi et al., *Br J. Ophthalmol*. February 10 [Epub ahead of print] (2009); Yodoi et al. *Am J. Ophthalmol*. 147, 816-824 (2009)) and some adverse effects might be misattributed to disease progression. In contrast to VEGF-A blockade, neither CCR3 Ab nor CCR3 receptor antagonist induced retinal toxicity in wild-type mice as confirmed by fundus imaging and electrophysiological function. Vegfa deletion is embryonically lethal (Carmeliet et al., *Nature*. 380, 435-439 (1996); Ferrara et al., *Nature*. 380, 439-442 (1996)) and conditional ablation of Vegfa in the RPE induces profound retinal degeneration and visual dysfunction (Marneros et al., *Am J. Pathol*. 167, 1451-1459 (2005). In contrast, the Ccr3$^{-/-}$ mouse retina was normal in appearance and electrophysiological function.

Discussion

CCR3 targeting is useful for early detection (using biocompatible quantum dots or other bioimaging fluorochromes such as near infrared dyes) and treatment of CNV (by receptor or ligand targeting) superior to current standard of care. CCR3 bioimaging is useful in individuals with RPE pigmentary disturbances and multiple subretinal lipoproteinaceous deposits known as drusen or fellow eye involvement with clinically evident CNV, as they are known to be at high risk for developing CNV (Bressler et al., *Arch Ophthalmol*. 108, 1442-1447 (1990); Maguire et al. *Arch Ophthalmol*. 115, 741-747 (1997). Similar techniques are also useful in non-invasively bioimaging other metabolic or molecular markers to provide information about disease pathogenesis or activity. For example, metabolic or molecular markers in tissues of the eye can be detected by contacting the tissue with an agent specific for that metabolic or molecular marker wherein the agent is labeled with a NIRF or Qdot and the label is detected by using angiography techniques that are well-known in the art.

Several strategies have yielded molecular markers that are preferentially expressed on proliferating endothelial cells such as those in tumor vasculature (St Croix et al., *Science* 289, 1197-1202 (2000); Zhang et al., *Science* 276, 1268-1272 (1997)) however, CCR3 has not been identified in any of these reports. Therefore, our studies identify CCR3 as a novel marker of pathological angiogenesis and as a functional target in neovascular AMD.

Thus, an aspect of this invention is a method for detecting subclinical CNV comprising contacting the choroid of a subject with an agent that specifically binds to CCR3 or to eotaxin 1, 2 or 3, and then assaying the choroid for binding of the agent to vessels in the choriod, wherein binding of the agent to vessels in the choroid is indicative of subclinical CNV. Subclinical as used herein refers to subjects who do have CNV invasion of the retina. Agents that specifically bind to CCR3 or to eotaxin 1, 2 or 3 include, e.g., CCR3- or eotaxin-specific antibody or antibody fragments, eotaxins 1, 2, or 3 and fragments of eotaxin 1, 2 or 3 that bind to CCR3; or peptides or aptamers that specifically bind to CCR3 or eotaxin 1, 2 or 3; or a CCR3-specific small molecule inhibitor, see for example U.S. Publication No. 20070190055 for a description of numerous small molecule inhibitors for the CCR3 receptor have been developed and can be used in the present invention. See also U.S. Pat. Nos. 6,806,061 and 6,207,155, and in U.S. published applications 20050191702, 20050069955, and 20020147312 for exemplary antibodies which specifically bind and inhibit the CCR3 receptor and U.S. Pat. Nos. 6,946,546 and 6,635,251, and in U.S. published applications 20040191255 and 20040014132 for exemplary antibodies, which specifically bind and inhibit eotaxin and eotaxin-2.

Antibodies and antibody fragments specific for CCR3 or eotaxins can be generated using any number of techniques well-known in the art. For example, for preparation of monoclonal antibodies, any technique which provides for the production of antibody molecules by continuous cell lines in culture may be used. For example, the hybridoma technique originally developed by Kohler and Milstein (*Nature* 256: 495-497 (1975)), as well as the trioma technique, the human B-cell hybridoma technique (Kozbor et al., *Immunology Today* 4:72 (1983)), and the EBV-hybridoma technique to produce human monoclonal antibodies (Cole et al., in "Monoclonal Antibodies and Cancer Therapy," Alan R. Liss, Inc. pp. 77-96 (1985)) and the like are within the scope of the present invention.

The monoclonal antibodies for therapeutic use may be human monoclonal antibodies or e.g., chimeric human-mouse (or other species) monoclonal antibodies. Human monoclonal antibodies may be made by any of numerous techniques known in the art (e.g., Teng et al., (1983) *Proc. Natl. Acad. Sci. U.S.A.* 80:7308-7312; Kozbor et al., (1983) *Immunology Today* 4:72-79; Olsson et al., (1982) *Meth. Enzymol*. 92:3-16). Chimeric antibody molecules may be prepared containing a mouse antigen-binding domain with human constant regions (Morrison et al., (1984) *Proc. Natl. Acad. Sci. U.S.A.* 81:6851, Takeda et al., (1985) *Nature* 314:452). Various procedures known in the art may be used for the production of polyclonal antibodies to epitopes of CCR3. For the production of antibody, various host animals can be immunized by injection with CCR3 protein, or fragment or derivative thereof, including but not limited to rabbits, mice, rats, etc. A molecular clone of an antibody to a CCR3 epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof. such fragments include but are not limited to: the F(ab')$_2$ fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent. See also, e.g., Cabilly et al., U.S. Pat. No. 4,816,567; Cabilly et al., European Patent No. 0,125, 023. B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

The agent may be conjugated to a detectable label. A detectable label is a moiety, the presence of which can be ascertained directly or indirectly. The detectable label may be, e.g., a radioisotope, a bioimaging fluorochrome, a contrast agent, or a gaseous agent. The agent may be e.g., a fluorescently labeled CCR3-specific antibody or antibody fragment, e.g., a CCR3-specific Fab or CCR3 specific peptide or aptamer. The agent may be conjugated to a bioimaging fluorochrome, e.g., a near infrared dye or semiconductor nanocrystals "quantum dots" and iron oxide nanocrystals. Those of ordinary skill in the art will know of suitable labels for binding to the agents used in the methods described herein, or will be able to ascertain such, using routine experimentation. The coupling of these labels to the agents used in the methods of the invention may be accomplished using standard techniques well-known to those of ordinary skill in the art. For example, nanoparticle probes have been used as labels in biological systems and for bioimaging (Akerman et al., *Proc Natl Acad Sci USA* 2002, 99:12617; Santra et al., *Analytical Chemistry*, 2001, 73:4988; Santra et al., *Journal of Biomedical Optics*, 2001, 6:160; Ben-Ari et al., *Journal of the National Cancer Institute*, 2003, 95:502; Panyam et al., *International Journal of Pharmaceutics*, 2003, 262:1); diagnostic (Brigger et al., *Adv Drug Deliv Rev*, 2002, 54:631; Alivisatos, *Scientific American*, 2001, 285:66), and therapeutic purposes (Emerich et al., *Expert Opinion on Biological Therapy* 2003, 3:655; Douglas et al., *Crc Critical Reviews in Therapeutic Drug Carrier Systems*, 1987, 3:233; Holm et al., *Molecular Crystals and Liquid Crystals*, 2002, 374:589). Diagnostic neuroimaging techniques such as angiography, CT (computed tomography) and MRI are well-known and widely used to monitor changes in anatomy and disease diagnosis (Hildebrandt et al., Clinical Immunology, 2004, 111:210; Dzik-Jurasz et al., *British Journal of Radiology*, 2004:77, 296; Costouros et al., *Journal of Cellular Biochemistry*, 2002:72; Langer et al., World *Journal of Surgery*, 2001, 25:1428; Smith et al., *Journal of Neurotrauma*, 1995, 12:573; Kreel et al., *Postgraduate Medical Journal*, 1991, 67:334). Contrast agents are often administered to patients, to help delineate pathological from healthy tissue. Contrast agents for angiography and CT scans are radio-opaque, which allow clear visualization of the contrast under an X-ray source. Iodinated chemical compounds such as iohexyl (also called OMNIPAQUE™) and iodixanol (also called VISIPAQUE™) are routinely used as X-ray contrast agents. They consist of electron dense iodine atoms, which show contrast under an X-ray. MRI contrast agents such as Gadoteridol, (Gd-HP-DO3A, a gadolinium chelate complex, also known as PROHANCE™) and mangafodipir trisodium (a manganese chelate complex, also known as TESLASCAN™) are usually paramagnetic. Both gadolinium and manganese atoms contain unpaired electrons, which account for paramagnetic behavior and resultant MRI contrast. See also U.S. Publication No. 20070269382 for a description of nanoparticles and their use for multifunctional bioimaging.

Another aspect of this invention is a method for treating CNV in a subject in need thereof comprising administering to the subject a CCR3 antagonist in an amount sufficient to inhibit progression of CNV. "Treating CNV in a subject" includes e.g., stopping, slowing or reversing the progression of CNV in the subject. In one aspect of the invention the retina of the subject is not invaded by CNV but CNV is detected in the choroid, e.g., CCR3 expression is detected in vessels in the choroid. The CCR3 antagonist may be, e.g., a CCR3 neutralizing antibody or CCR3 neutralizing antibody fragment or a peptide that competes with a natural ligand for binding to CCR3 or a peptide or low molecular weight compound having activity which inhibits binding of CCR3 ligands to CCR3 on target cells. The CCR3 antagonist may also be a peptide that specifically binds to CCR3, wherein the peptide is conjugated to toxin or cytostatic agent that kills or inhibits the growth of cells expressing CCR3. The CCR3 neutralizing antibody fragment may be e.g., a CCR3-specific Fab. The CCR3-specific antibody or antibody fragment may be conjugated to a compound suitable for bioimaging, e.g., bioimaging fluorochrome such as a near-infrared fluorophore ("NIRF") or quantum dot.

A subject in need thereof may be a subject at risk for developing or suspected of having choroidal neovascularization. The subject may be e.g., a subject at risk for developing age related macular degeneration or an individual with RPE pigmentary disturbances, multiple subretinal lipoproteinaceous deposits or fellow eye involvement with clinically evident CNV. In one aspect of the invention, the retina of a subject at risk for developing or suspected of having choroidal neovascularization is not invaded by CNV.

In the methods of this invention the agent which specifically binds to CCR3 or to eotaxin 1, 2 or 3, or the CCR3-specific antagonist may be administered systemically or locally. For example, the agent or CCR3-specific antagonist may be administered intravenously, intrathecally, intraarterially, intranasally, orally, subcutaneously, intraperitoneally, or by local injection or surgical implant in an amount sufficient to detect CCR3 on choroid vessels or to inhibit CNV progression.

The invention also relates to a method for evaluating the risk of a subject for developing retinal CNV. In one aspect of the invention, a subject is assayed for CCR3 expression in choroid vessels, wherein expression of CCR3 in choriod vessels is indicative of choridal CNV or an elevated risk for developing retinal CNV. In another aspect of this invention, the level of CCR3 expression is compared to the expression level in the choroid of subjects who are not at risk for developing or suspected of having choroidal neovascularization Also an aspect of this invention is a method for assaying a pre-selected agent for inhibition of choroid CNV in a subject comprising detecting expression of CCR3 in the choroid of the subject by bioimaging before and after treatment with an agent and comparing expression levels or localization of CCR3 in the choroid before and after treatment, wherein a reduction in CCR3 expression in the choroid or a change in the localization of CCR3 in the choroid is indicative of inhibition of CNV by the agent. The subject may e.g., have CNV in the choroid and/or the retina of the subject may also have CNV.

EXAMPLES

Methods

Mouse model of CNV. Laser photocoagulation (OcuLight GL, Iridex Corporation) was performed on mouse eyes to induce CNV, and CNV volumes were measured 7 days after injury by scanning laser confocal microscope (TCS SP, Leica) as previously described (Kleinman, et al., Nature. 452, 591-597 (2008)). Drug injections. Rat IgG2a neutralizing antibody against mouse CCR3 (R&D Systems), control rat IgG2a (Serotec), goat neutralizing antibody against mouse CCL11 (R&D Systems), goat neutralizing antibody against mouse CCL24 (R&D Systems), control goat IgG (Jackson Immunoresearch), or (S)-Methyl-2-naphthoylamino-3-(4-nitrophenyl)propionate (SB328437; Calbiochem) dissolved in DMSO were injected into the vitreous humor using a 33-gauge double-calibre needle (Ito Corporation) once, immediately after laser injury as previously described (Kleinman, et al., (2008) supra).

CCR3 bioimaging. F(ab) fragments were created from monoclonal IgG2a antibody raised against the extracellular domain of murine CCR3 (R&D Systems) and an isotype rat IgG2a (R&D Systems) using a commercially available papain-based kit (Pierce). Recovered fragments were conjugated with quantum dots (Invitrogen, QDot-800) and resuspended in sterile PBS. $Ccl2^{-/-} \times Ccr2^{-/-}$ mice were administered 100 µg of tagged CCR3 F(ab) or isotype F(ab) via tail vein injection after acquiring baseline fluorescent imaging using a Topcon retinal camera (TRC-50IX). Serial images were then acquired at 1, 4, and 12 h after which eyes were harvested and frozen in OCT for immunofluorescent analyses. Retinal images were analyzed (ImageNet, Topcon) by comparison to baseline and fluorescein angiographic data. Hyperfluorescent areas were then cropped, equally thresholded, and pseudocolored (Photoshop CS3, Adobe). Sections from QDot-conjugated CCR3 or rat IgG2a isotype F(ab) injected animals were fixed in 4% paraformaldehyde and blocked with 5% normal donkey serum/5% goat serum in PBS, stained with rat anti-mouse CD31 (BD Biosciences) and either rabbit anti-mouse CCR3 (Santa Cruz) or rabbit anti-Ki67 (Abcam) followed by appropriate fluorescent secondary antibodies (Alexa Fluor 488/594, Invitrogen), and evaluated by confocal laser scanning microscopy (Leica SP-5).

Methods

Human tissue. Choroidal neovascularization (CNV) tissue was excised from patients with age-related macular degeneration (AMD) who had no prior treatment for CNV. Retinal fibrosis tissue was excised from patients with a diagnosis of epiretinal membrane formation. Donor eyes from patients with atrophic AMD without CNV and patients without AMD were obtained from eye banks. Eyes with choroidal melanoma were obtained by surgical enucleation. The study followed the guidelines of the Declaration of Helsinki. Institutional review boards granted approval for allocation and histological analysis of specimens.

Animals. All animal experiments were in accordance with the guidelines of the University of Kentucky IACUC and the Association for Research in Vision and Ophthalmology. C57BL/6J and $Kit^{W-v}/Kit^{W-v}$ mice were purchased from The Jackson Laboratory. $Ccr3^{-/-}$, $Ccl11^{-/-}$, $Ccl24^{-/-}$, $Ccl11^{-/-} \times Ccl24^{-/-}$, and Δdbl GATA mice have been previously described (Humbles et al., Science. 305, 1776-1779 (2004); Pope et al. J. Immunol. 175, 5341-5350 (2005); Humbles et al. Proc Natl Acad Sci USA. 99, 1479-1484 (2002); Rothenberg et al., J Exp Med. 185, 785-790 (1997)). $Ccl2^{-/-} \times Ccr2^{-/-}$ mice were generated by interbreeding "single knockout" mice described previously (Ambati et al., Med. 9, 1390-1397 (2003)).

Drug injections. Rat IgG2a neutralizing antibody against mouse CCR3 (R&D Systems), control rat IgG2a (Serotec), goat neutralizing antibody against mouse CCL11 (1 µg; R&D Systems), goat neutralizing antibody against mouse CCL24 (5 µg; R&D Systems), control goat IgG (Jackson Immunoresearch), or (S)-Methyl-2-naphthoylamino-3-(4-nitrophenyl) propionate (SB328437; Calbiochem) dissolved in DMSO were injected into the vitreous humor of mice using a 33-gauge double-calibre needle (Ito Corporation) once, immediately after laser injury as previously described (Kleinman, et al., (2008) supra).

Flow cytometry. Rat antibody against mouse CCR3 (1:250; Santa Cruz) coupled with PE-donkey antibody against rat IgG (1:250; Jackson Immunoresearch) or AlexaFluor647-conjugated rat antibody against mouse CCR3 (10 µg/ml; BD Biosciences) were used to quantify cell surface receptor expression on choroidal endothelial cells, defined by $CD31^+VEGFR-2^+$ expression, gated by FITC-conjugated rat antibody against mouse CD31 (20 µg/ml; BD Biosciences) and PE-conjugated rat antibody against mouse VEGFR-2 (20 µg/ml; BD Biosciences). Macrophages, neutrophils, eosinophils and mast cells were defined as $F4/80^+CD11c^-$, $Gr-1^+F4/80^-$, $CCR3^{hi}CD3^-CD117^{int}CD49d^+$ and $CCR3^{int}CD3^-CD117^{hi}CD49d^+$ cells, respectively. DNA content for cell cycle was analyzed after incubation with propidium iodide (0.05 mg/ml; Molecular Probes) containing 0.1% Triton X-100 and RNase A (0.1 mg/ml; Roche). Samples were analyzed on a LSRII (Becton Dickinson).

Immunolabeling. Immunofluorescent staining was performed with antibodies against human CCR3 (rat monoclonal, R&D Systems) or human CD31 (mouse monoclonal, Dako) and identified with Alexa 488 (Molecular Probes) or Cy3 secondary antibodies (Jackson ImmunoResearch). Immunohistochemical staining with the primary antibodies specific for human eotaxins-1, 2 and 3 (mouse monoclonal, R&D Systems) was performed using horseradish peroxidase. Laser injured mouse eye sections were stained with antibodies against mouse CCL11 or CCL24 (both R&D Systems) along with antibody against mouse CD31 (BD Biosciences) and visualized with FITC or Cy3 secondary antibodies. Images were obtained using Leica SP5 or Zeiss Axio Observer Z1 microscopes.

Tube formation assay. 96-well plates were coated with Growth Factor Reduced Matrigel (BD Biosciences) mixed with rat neutralizing antibody against human CCR3 (20 µg/ml, R&D Systems) or control rat IgG2a (Invitrogen) and allowed to solidify in the incubator at 37° C. for 45 min. Human choroidal endothelial cells $(CECs)_{44-47}$ were plated on top of the Matrigel at $2.25 \times 10^4/cm^2$ in EBM-2 basal media (Cambrex) containing 1% FBS with CCR3 antibody or rat IgG2a at the above concentrations and allowed to grow overnight. Tube formation was analyzed by counting the number of cell junctions per mm2.

Proliferation assay. Human CECs were synchronized for cell cycle state by first cultivating them in EGM2-MV media (Lonza) supplemented with 10% FBS (Gibco) to achieve complete confluence and then by overnight serum starvation in MCDB131 media (Gibco) with 0.1% FBS. They were passaged to 96-well plates at a density of 5,000 cells per well, followed by stimulation for 24 h with eotaxin-1, 2 or 3 (10 ng, 100 ng and 2 µg per ml, respectively; Peprotech) in MCDB131 media with 0.1% FBS. After 24 h, cell viability was measured with BrdU ELISA (Chemicon) according to manufacturer's instructions.

F-actin Polymerization Assay. Human CECs were seeded in black-walled 96-well plates and grown to 70-80% confluence in fully supplemented EGM-2MV. Cultures were serum starved overnight in basal media and then stimulated with recombinant human eotaxin-1 (10 ng/ml), eotaxin-2 (100 ng/ml), eotaxin-3 (2 µg/ml) (Peprotech), or vehicle control (PBS). At 0, 10, 30, 60, or 120 sec time-points, cells were fixed in 3.7% paraformaldehyde for 10 min, washed, permeabilized in PBS with 0.1% Triton-X, and then stained with rhodamine labelled Phalloidin (1:200, Invitrogen) per manufacturer's recommendations. Plates were analyzed on a fluorescent plate reader (Synergy 4, Biotek) followed by fluorescent microscopy (Nikon E800).

Migration Assay. Eotaxins-1, -2, -3 were reconstituted in 0.1% bovine serum albumin (BSA) and then mixed with Matrigel diluted 1:1 with serum free endothelial basal media (EBM-2; Lanza). 500 µl of EBM-2 was added to each well of a 24-well plate followed by a 6.5 mm diameter Transwell insert (8 µm pores; Corning). Human CECs in EBM-2 were prestained with Vybrant DiO (Invitrogen) for 30 min at 37° C. and seeded into the inserts at 50,000 cells per 200 µl of serum free EBM-2 media. The plates were allowed to incubate for 16 h at 37° C., 5% $CO_2$. The migrated cells were imaged with an Olympus CK40 microscope and Olympus DP71 camera.

Rac-1 activation. Human CECs were cultured in EGM-2 MV containing 5% FBS. Prior to starting the assay, cells were serum starved with basal medium (MCDB131) supplemented with 1% FBS overnight. Cells were stimulated for designated times with Eotaxin-1, 2 and 3 (10 ng/ml, 100 ng/ml and 2 µg/ml respectively). Equal amounts of lysates (500 µg) were incubated with GST-Pak1-PBD agarose beads (Upstate) to pull-down active GTP-bound Rac-1 at 4° C. for 1 h with rotation. The samples were subsequently analyzed for bound Rac-1 by western blot analysis using an anti-Rac-1 antibody (Upstate).

Electroretinography. Mice were dark adapted overnight and then anesthetized. Both eyes were positioned within a ColorBurst Ganzfeld stimulator (Diagnosys). Espion software (Diagnosys) was used to program a fully automated flash intensity series from which retinal responses were recorded.

All references cited in this disclosure are incorporated by reference to the same extent as if each reference had been incorporated by reference in its entirety individually.

While the invention has been described in detail and with reference to specific embodiments thereof, it will be apparent to one skilled in the art that various variations and modifications can be made therein without departing from the sprit and scope thereof. All such variations and modifications are intended to be included within the scope of this disclosure and the present invention and protected by the following claims.

We claim:

1. A method for detecting subclinical choroidal neovascularization ("CNV") comprising contacting a choroid with an agent that specifically binds CCR3 and assaying the choroid for binding of the agent to vessels in the choroid, wherein binding of the agent to vessels in the choroid is indicative of subclinical CNV.

2. The method of claim 1 wherein the agent is a CCR3 specific antibody; a CCR3-specific antibody fragment; eotaxin 1, eotaxin 2 or eotaxin 3; a fragment of eotaxin 1, eotaxin 2 or eotaxin 3 that binds to CCR3; a peptide or aptamer that specifically binds to CCR3, eotaxin 1, eotaxin 2 or eotaxin 3; or a CCR3-specific small molecule inhibitor.

3. The method of claim 2 wherein the agent is conjugated to a detectable label.

4. The method of claim 2 wherein the label is a bioimaging fluorochrome.

5. The method of claim 4 wherein the bioimaging fluorochrome is a near infrared dye or quantum dot.

6. The method of claim 1 wherein the agent is a detectable CCR3-specific antibody or antibody fragment.

7. The method of claim 6 wherein the CCR3-specific antibody fragment is a CCR3-specific Fab.

8. The method of claim 7 wherein the CCR3-specific Fab is conjugated to a bioimaging fluorochrome.

9. The method of claim 1 wherein the choroid is in or from a subject at risk for developing or suspected of having choroidal neovascularization.

10. The method of claim 9 wherein the subject is a subject at risk for developing age-related macular degeneration.

11. The method of claim 9 wherein the subject is an individual with retinal pigmented epithelium ("RPE") pigmentary disturbances, multiple subretinal lipoproteinaceous deposits or fellow eye involvement with clinically evident CNV.

* * * * *